United States Patent
Lhermitte et al.

(10) Patent No.: US 7,132,535 B2
(45) Date of Patent: Nov. 7, 2006

(54) PROCESS FOR PREPARING HEXAHYDROPYRIDAZINE-3-CARBOXYLIC ACID DERIVATIVES

(75) Inventors: Hervé Lhermitte, Paris (FR); Charles-Henri Vincent, Precy sur Oise (FR); Christian Picherit, Boussemont (FR)

(73) Assignee: Isochem, Paris (FR)

( * ) Notice: Subject to any disclaimer, the term of this patent is extended or adjusted under 35 U.S.C. 154(b) by 73 days.

(21) Appl. No.: 10/826,031

(22) Filed: Apr. 15, 2004

(65) Prior Publication Data

US 2004/0210053 A1 Oct. 21, 2004

(30) Foreign Application Priority Data

Apr. 16, 2003 (FR) .................... 03 04763

(51) Int. Cl.
*C07D 237/02* (2006.01)
(52) U.S. Cl. ....................... 544/224; 564/464
(58) Field of Classification Search ................ 544/224
See application file for complete search history.

(56) References Cited

U.S. PATENT DOCUMENTS 4,988,813 A * 1/1991 Taylor et al. ............... 544/279
6,632,942 B1 * 10/2003 Robidoux et al. .......... 540/500

FOREIGN PATENT DOCUMENTS

WO      9955724      11/1999

OTHER PUBLICATIONS

Bioorganic & Medicinal Chemistry 10, (2002) 953-961 CYCLIC . . . RH-5849.

J. Org. Chem, vol. 24, 1959, pp. 724-725 Alkylation of Some Diacyclhydrazines, Hinman et al.

\* cited by examiner

*Primary Examiner*—Kahsay Habte
(74) *Attorney, Agent, or Firm*—Charles A. Muserlian

(57) ABSTRACT

According to the process of the invention, the hexahydropyridazine-3-carboxylic acid derivatives are prepared by reacting a compound of formula (II)

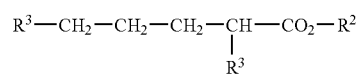

with a compound of formula (III)

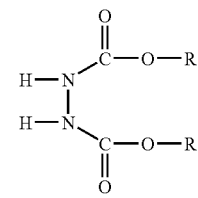

in the presence of a base with a pK of greater than or equal to 8.5, in a ketone organic solvent, to obtain an intermediate compound that is not isolated and that is treated with a basic aqueous medium.

By means of this process, the derivatives are obtained more quickly and more economically.

15 Claims, No Drawings

PROCESS FOR PREPARING HEXAHYDROPYRIDAZINE-3-CARBOXYLIC ACID DERIVATIVES

The present invention relates to an improved process for preparing hexahydropyridazine-3-carboxylic acid derivatives.

Hexahydropyridazine-3-carboxylic acid and its derivatives are compounds that are very useful as intermediates for preparing medicinal products.

Several processes for synthesizing them have been proposed. Patent application WO 99/55724 describes a process for preparing hexahydropyridazine-3-carboxylic acid bearing an arylmethyloxycarbonyl substituent in position 1 starting with an alkyl 2,5-dihalopentanoate and bisarylmethyl 1,2-hydrazine-dicarboxylate.

The process proceeds in 2 steps. In the first step, the tetrahydro-1,2-bisarylmethyl intermediate is first formed, which is isolated and is then subjected to a basic treatment to obtain the desired acid derivative.

The reaction scheme is as follows:

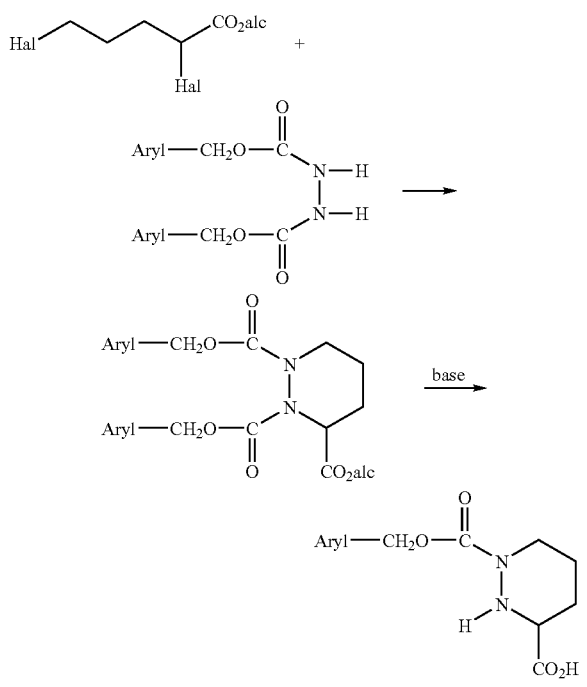

The implementation of this process presents drawbacks.

Very large amounts of solvents are used. Some of these solvents are carcinogenic, such as diglyme, the solvent for the first step. Others are highly flammable, such as ethers, for instance isopropyl ether, which is used to isolate the compounds. Others are harmful to the health of the operatives and to the environment, such as ethanol, the solvent for the reaction of the second step, or chlorinated solvents, for instance dichloromethane, which are used for the extractions of the compounds.

These large amounts of solvent require the use of bulky reactors, which entail numerous manipulations to remove them or to perform exchanges. The labor time and time of residence in the reactors and the other installations are thus very long. This also results in losses of yield and an unsatisfactory purity of the compounds. Furthermore, according to this process, certain purifications of the compounds are performed by chromatography on a solid support, which is a method that is not industrially viable.

There was consequently a need to improve the conditions for the implementation of the process in order to obtain the desired derivatives more quickly and more economically.

One subject of the invention is a process for preparing the hexahydropyridazine-3-carboxylic acid derivatives of formula (I)

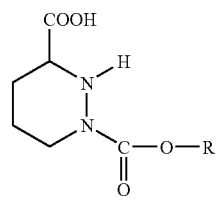

in which R represents a saturated or unsaturated, substituted or unsubstituted alkyl radical, a substituted or unsubstituted aralkyl radical or a substituted or unsubstituted aryl radical, characterized in that a compound of formula (II)

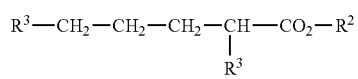

in which $R^2$ represents a substituted or unsubstituted alkyl radical, and $R^3$ represents a nucleofugal organic group, is reacted with a compound of formula (III)

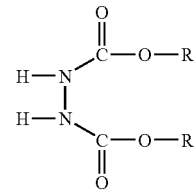

in which R has the above meaning, in the presence of a base with a pK of greater than or equal to 8.5, in an organic solvent chosen from ketones, to obtain the tetrahydro-1,2,3-pyridazine-tricarboxylate intermediate compound of formula (IV)

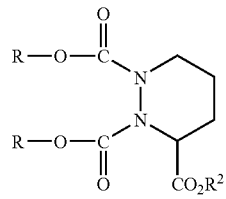

in which R and $R^2$ have the above meanings, which is not isolated and which is treated with a basic aqueous medium, to obtain the hexahydropyridazine-3-carboxylic acid derivatives of formula (I).

According to this process, the amounts of organic solvent used are very small. Only the first reaction is performed in the presence of an organic solvent of ketone type, which is consequently nontoxic.

The intermediate tetrahydro-1,2,3-pyridazine-tricarboxylate compound of formula (IV) is not isolated from the medium. Consequently, no treatment with an acid and no extraction with an organic solvent, as are performed in example 1d) page 9 of patent application WO 99/55724, are necessary.

The solvent to perform the second reaction does not pose any problems since it is water. This thus avoids the use of an alcoholic solvent that subsequently has to be removed, as is the case in example 1, paragraph e) pages 9 and 10 of the prior art document cited above.

The production efficiency according to the process of the invention is thus considerably increased.

Moreover, the recovery of the final derivative of formula (I) is simply performed by crystallization from a water/solvent two-phase medium. The numerous extractions with dichloromethane performed according to the prior-art process are thereby avoided.

The process according to the invention allows the derivatives of formula (I) to be obtained either in their racemic form or in their optically active R or S form.

The compounds of formulae (II) and (III) used as starting materials are known compounds that are commercially available or that may be prepared according to known methods.

In the compounds of formulae (I) and (III), R, when it represents an alkyl radical, is in particular a $C_1$ to $C_8$ radical. It may be saturated or unsaturated, for instance the allyl or vinyl radical. Substituents that may especially be mentioned include halogen atoms such as chlorine, preferably not in position 1.

When R represents an aralkyl radical, it is preferably a radical of formula —$CH_2$—$R^1$ in which $R^1$ is a substituted or unsubstituted aryl radical.

The radical $R^1$ may bear one or more substituents chosen especially from halogen atoms, such as chlorine, and alkyl radicals, in particular of $C_1$ to $C_3$.

R may also represent an aryl radical optionally bearing one or more substituents chosen especially from alkyl radicals, in particular of $C_1$ to $C_4$, alkoxy radicals, in particular of $C_1$ to $C_4$, phenoxy radicals and halogen atoms, such as chlorine and fluorine.

The term "aryl radical" means a monocyclic or polycyclic hydrocarbon-based aromatic radical, the rings possibly being fused, in particular a $C_6$ to $C_{14}$ radical such as the naphthyl or biphenyl radical, preferably the phenyl radical.

$R^2$ may represent a linear or branched, substituted or unsubstituted alkyl radical, especially of $C_1$ to $C_{20}$, in particular of $C_1$ to $C_8$ and preferably of $C_1$ to $C_4$. Substituents of $R^2$ that may especially be mentioned include alkoxy radicals, in particular methoxy and ethoxy.

Examples of radicals $R^2$ that may be mentioned include isopropyl and isobutyl radicals. Methyl and ethyl radicals are suitable for use.

$R^3$ represents an organic group that can be easily separated from the rest of the molecule under the conditions of the process, such as a a halogen atom or mesylate or tosylate group.

As halogen atoms represented by $R^3$, mention may be made of chlorine, bromine or iodine atoms and preferably chlorine or bromine atoms.

It has been found that an improvement of the prior-art process consists in reacting the compound of formula (II) with the compound of formula (III) in an organic solvent medium chosen from ketones. Ketones that may be mentioned include methyl ethyl ketone, methyl isobutyl ketone, methyl tert-butyl ketone and diisopropyl ketone, used alone or as a mixture.

Acetone is the preferred solvent.

Compound (II) is generally used in an amount of between 1 and 1.5 and preferably between 1 and 1.1 mol per mole of compound of formula (III).

The reaction takes place in the presence of a base whose $pK_a$ is greater than or equal to 8.5. Bases that may be mentioned include alkali metal carbonates, in particular of sodium or potassium, and tertiary amines, for instance triethylamine or N-methylmorpholine. The base is preferably present in the medium in an amount of between 2 and 3 mol per mole of the compound of formula (II).

It is possible, in order to facilitate the reaction, to add to the reaction medium a solid-liquid phase-transfer catalyst such as a tetraalkylammonium salt, or a surfactant.

The reaction temperature depends on the solvent used. It is generally between 50° C. and 100° C. A temperature of between 55° C. and 65° C. is preferably chosen. The reaction time also depends on the solvent used. It is generally from about 25 to 35 hours.

In contrast with the process according to the prior art, the intermediate hydrazine derivative formed, of formula (IV) is not isolated. It has been found that it can advantageously be made to react under new conditions without it being necessary to isolate it. The numerous treatments and extractions that are obligatory when it is desired to recover it, and the losses of products resulting therefrom, are thus avoided.

The compound of formula (IV) is thus treated with a basic aqueous medium. Preferably, the aqueous medium should be highly basic; in particular, the pH should be greater than or equal to 12.

The basicity is provided by a mineral or organic compound. A mineral base chosen from alkali metal hydroxides, in particular sodium hydroxide and potassium hydroxide, is suitable for use. As organic compounds providing high basicity, mention may be made of alkali metal or alkaline-earth metal alkoxides, for instance sodium or potassium methoxide, ethoxide or tert-butoxide.

The amount of base to be used is generally between 3 and 6 molar equivalents relative to compound (III). An amount of 4 to 5 molar equivalents is suitable for use. The amount of base chosen may be supplied in one or more portions.

Preferably, for practical reasons, the alkali metal hydroxides are used in aqueous solution.

It has been found that it is much more advantageous to perform the second reaction using water as solvent.

The amount of water used is generally between 1 and 10 liters per kilogram of compound (III).

The majority of the ketone solvent used for the first reaction is generally removed, for example by distillation, before performing the second reaction. Preferably, all of the solvent is removed.

The temperature of the second reaction is generally between 20° C. and 60° C. and preferably between 25° C. and 55° C. Different successive temperature stages may be applied within these ranges. The reaction time is generally from 2 to 12 hours.

It has also been found that the compound of formula (I) can be recovered very easily by crystallizing it directly from the reaction medium, despite the presence of the alcohol, in particular the aralkyl alcohol, formed during the last reaction. To do this, the reaction medium is mixed with an acid and an organic solvent in which compound (I) is insoluble. Preferably, the solvent is used before the acid.

Acids that may be mentioned include acetic acid or formic acid and, preferably, hydrochloric acid or sulfuric acid.

The acid is used in an amount that is sufficient to bring the pH of the medium to between 0.5 and 2 and preferably in the region of 1. Hydrochloric acid is suitable for use.

As solvents that do not dissolve the compounds of formula (I), mention may be made in particular of alcohol-diluting solvents, which are solvents that are generally sparingly polar, such as aromatic hydrocarbons, aliphatic hydrocarbons, which are preferably nonchlorinated, ethers and acetates.

Toluene and xylenes are preferably used.

It is unnecessary to use a large amount of organic solvent. Generally, this amount is between 1 and 5 liters per kilogram of compound (III).

The compounds of formula (I) are then in suspension in the organic phase. This phase may be separated from the aqueous phase according to standard methods, for example by decantation, and the compounds readily recovered especially by filtration.

The process according to the invention makes it possible to obtain the derivatives of formula (I) in good yields, which are often greater than or equal to 70% and with a high purity determined by HPLC of greater than 97%.

The example that follows illustrates the invention without, however, limiting it.

EXAMPLE 1

1 kg (3.3 mol) of 1,2-dibenzyloxycarbonyl-hydrazine, 0.025 kg of tetrabutylammonium bromide, 1 kg (2.2 eq) of potassium carbonate ($K_2CO_3$) as a fine powder and 5 l of acetone are placed in an equipped 8-liter reactor and the mixture is stirred.

1 kg (3.65 mol) of methyl 2,5-dibromovalerate are then added and the mixture is heated at the reflux temperature of the acetone for 24 hours.

The mixture is cooled to 0° C. The solids are separated out by suction-filtration.

The liquid medium is then concentrated under reduced pressure until an oily concentrate is obtained.

1 l of water is then added, followed by addition of 1.66 l of 30% sodium hydroxide solution, while keeping the temperature at 40° C., and the reaction mixture is stirred for 5 to 7 hours at this temperature.

2.6 l of toluene are added, followed by slow addition of 1.4 l of 36% hydrochloric acid to obtain a pH of about 1.

The 1-benzyloxycarbonylhexahydropyridazin-3-yl-carboxylic acid of formula (I) crystallizes.

It is filtered off by suction, washed with toluene and then with water, and dried. 0.62 kg of dry acid (overall yield 71%) with a purity, determined by HPLC, of greater than 97.0% is thus collected.

What is claimed is:

1. A process for preparing a hexahydropyridazine-3-carboxylic acid derivative of the formula

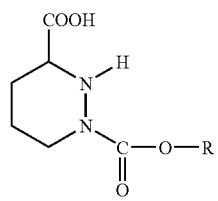

I wherein R is selected from the group consisting of saturated or unsaturated, substituted or unsubstituted alkyl, substituted or unsubstituted aralkyl substituted or unsubstituted aryl comprising reacting a compound of the formula

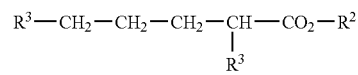

II wherein $R^2$ is substituted or unsubstituted alkyl and $R^3$ a nucleofugal organic group, with a compound of the formula

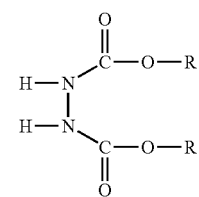

III whereas R has the above meaning, in the presence of a base with a $pK_a$ greater than or equal to 8.5, in an organic ketone solvent to a tetrahydro- 1,2,3-pyridazine-tricarboxylate intermediate compound of the formula

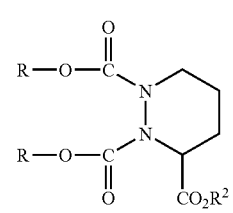

IV wherein R and $R^2$ have the above meanings, which is not isolated and which is treated with a basic aqueous medium, to obtain the hexahydropyridazine-3-carboxylic acid derivative of formula (I).

2. The process of claim 1, wherein the organic ketone solvent is selected from the group consisting of acetone, methyl ethyl ketone, methyl isobutyl ketone, methyl tert-butyl ketone and diisopropyl ketone, and mixtures thereof.

3. The process of claim 1 wherein the base used in the first reaction is selected from the group consisting of alkali metal carbonates and tertiary amines.

4. The process of claim 1 wherein the solvent is acetone.

5. The process of claim 1 wherein the base used in the first reaction is potassium carbonate.

6. The process of claim 1 wherein the base used for the second reaction is selected from the group consisting of alkali metal hydroxides and alkali metal or alkaline-earth metal alkoxides.

7. The process of claim 6 wherein the alkali metal hydroxides are used in aqueous solution.

8. The process of claim 1 wherein, for the second reaction, the temperature is 25° C. to 55° C. and the volume of water is 1 to 10 liters per kilogram of compound of formula (III).

9. The process of claim 8 wherein the reaction is performed by applying different successive temperature stages within the range.

10. The process of claim 1 wherein the compound of formula (I) is obtained in crystalline form by mixing the reaction medium with a solvent in which the compound of formula (I) is insoluble and which is a diluent for alcohols, and by adjusting the pH of the medium to 0.5 to 2 using an acid.

11. The process of claim 10 wherein the solvent is selected from the group consisting of aromatic hydrocarbons, aliphatic hydrocarbons, ethers and acetates.

12. The process of claim 10 wherein the acid is hydrochloric acid.

13. The process of claim 1 wherein $R^1$ is phenyl or naphthyl; and $R^2$ is of 1 to 4 carbon atoms.

14. The process of claim 13, wherein $R^1$ is phenyl, $R^2$ is methyl and $R^3$ is bromine.

15. The process of claim 1 wherein $R^3$ is selected from the group consisting of halogen, mesylate and tosylate.

* * * * *